US011219587B2

(12) United States Patent
Meyer et al.

(10) Patent No.: US 11,219,587 B2
(45) Date of Patent: Jan. 11, 2022

(54) COMPOSITION FOR LIGHTENING OR DYEING KERATIN FIBERS WITH A LOW AMOUNT OF ALKALIZING AGENT

(71) Applicant: Noxell Corporation, Hunt Valley, MD (US)

(72) Inventors: Axel Meyer, Schwalbach am Taunus (DE); Andrej Gross, Darmstadt (DE); Bjoern Hoffmann, Darmstadt (DE); Simon Paul Godfrey, Oberursel (DE); Lina Makavou-Jennen, Darmstadt (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 0 days.

(21) Appl. No.: 16/327,680

(22) PCT Filed: Sep. 14, 2017

(86) PCT No.: PCT/US2017/051654
§ 371 (c)(1),
(2) Date: Feb. 22, 2019

(87) PCT Pub. No.: WO2018/053195
PCT Pub. Date: Mar. 22, 2018

(65) Prior Publication Data
US 2019/0183762 A1    Jun. 20, 2019

(30) Foreign Application Priority Data
Sep. 14, 2016    (EP) ..................... 16188776

(51) Int. Cl.
| *A61Q 5/10* | (2006.01) |
| *A61K 8/41* | (2006.01) |
| *A61K 8/31* | (2006.01) |
| *A61K 8/22* | (2006.01) |
| *A61K 8/34* | (2006.01) |
| *A61K 8/90* | (2006.01) |
| *A61K 8/49* | (2006.01) |
| *A61K 8/38* | (2006.01) |

(52) U.S. Cl.
CPC .............. *A61K 8/41* (2013.01); *A61K 8/22* (2013.01); *A61K 8/31* (2013.01); *A61K 8/342* (2013.01); *A61K 8/347* (2013.01); *A61K 8/38* (2013.01); *A61K 8/411* (2013.01); *A61K 8/494* (2013.01); *A61K 8/90* (2013.01); *A61Q 5/10* (2013.01); *A61K 2800/88* (2013.01); *A61K 2800/882* (2013.01); *A61K 2800/884* (2013.01)

(58) Field of Classification Search
CPC .......... A61Q 5/10; A61K 8/411; A61K 8/415; A61K 8/22; A61K 8/342; A61K 8/41; A61K 8/347; A61K 8/31; A61K 47/44; A61K 2800/88; A61K 2800/882; A61K 2800/4324; A61K 2800/884
USPC ............................................. 8/405
See application file for complete search history.

(56) References Cited

U.S. PATENT DOCUMENTS 8,920,521 B1    12/2014    Benn
2014/0090184 A1    4/2014    Benn et al.

FOREIGN PATENT DOCUMENTS

| WO | WO 2014020147 A2 * | 2/2014 | ............... A61Q 5/10 |
| WO | WO-2014020147 A2 | 2/2014 | |
| WO | WO-2018053195 A1 | 3/2018 | |

OTHER PUBLICATIONS

"International Application Serial No. PCT/US2017/051654, International Search Report dated Oct. 30, 2017", 4 pgs.
"International Application Serial No. PCT/US2017/051654, Written Opinion dated Oct. 30, 2017", 8 pgs.
"European Application Serial No. 16188776.5, Communication Pursuant to Article 94(3) EPC dated Apr. 11, 2019", 5 pgs.
"European Application Serial No. 16188776.5, Response Filed Jul. 30, 2019 to Communication Pursuant to Article 94(3) EPC dated Apr. 11, 2019", 24 pgs.
"International Application Serial No. PCT/US2017/051654, International Preliminary Report on Patentability dated Mar. 28, 2019", 8 pgs.

* cited by examiner

Primary Examiner — Eisa B Elhilo
(74) Attorney, Agent, or Firm — Victoria Friedman; Dennemeyer & Associates, LLC

(57) ABSTRACT

An agent for dyeing keratin fibers comprises a composition A comprising at least one alkalizing agent, at least one oxidative dye precursor, at least one surfactant and at least one fatty substance free of carboxylic acid groups and a composition B comprising at least one oxidizing agent and at least one surfactant. The concentration of fatty substances free of carboxylic acid groups after mixing composition A and composition B is at least 20% by weight relative to the total weight of the mixed composition A and B. The concentration of alkalizing agent after mixing composition A and composition B is not more than 1.75% by weight relative to the total weight of the mixed composition A and B.

18 Claims, No Drawings

COMPOSITION FOR LIGHTENING OR DYEING KERATIN FIBERS WITH A LOW AMOUNT OF ALKALIZING AGENT

PRIORITY

This application is a U.S. National Stage Filing under 35 U.S.C. 371 from International Application No. PCT/US2017/051654, filed on Sep. 14, 2017, and published as WO 2018/053195 on Mar. 22, 2018, which application claims the benefit of priority from EP Patent Application No. 16188776.5, filed on Sep. 14, 2016, which is herein incorporated in its entirety by reference.

FIELD OF THE INVENTION

The invention provides an agent for dyeing keratin fibers, in particular human keratin fibers such as the hair, comprising a high concentration of fatty substances and a low concentration of alkalizing agent.

BACKGROUND OF THE INVENTION

The permanent alteration of the hair color by the application of hair dyes is well known. In order to provide the consumer with the shade and the intensity of the desired color, a complex chemical process is utilized. Permanent hair dyeing formulations typically comprise oxidative hair dye precursors, which can diffuse into the hair through the cuticle and into the cortex where they then react with each other and a suitable oxidizing agent to form the final dye molecules. Due to their larger size, the resultant molecules are unable to readily diffuse out of the hair during subsequent washing with water and/or detergents; hence delivering a consumer-desired permanency of color. This reaction typically takes place in an aggressive environment at approximately pH 10 in the presence of an alkalizing agent and an oxidizing agent. Typically an oxidizing composition comprising the oxidizing agent and a dye composition comprising the alkalizing agent and if present the oxidative dye precursors are mixed shortly before use. The consumer repeats this process regularly in order to maintain the desired hair color and shade and the intensity of color and to ensure continual, even coverage of the hair including coverage of new hair growth.

Hair dyeing involves the application of one or more oxidative dye precursors onto hair which results in the dyeing of hair fibers. The hair color may be changed subtly or dramatically, the root growth colored to match the remaining head of hair, effects introduced such as glitter, hair swatch effects or other sectional effects, or the same color "freshened up" to combat fade and/or wash-out. In modern times, the consumer has a wide variety of options for dyeing the hair (whether in the salon or at home) from direct dyes that wash out relatively quickly, hair make-up for applying glitter and/or hair swatch effects, to conventional (semi-) permanent dyeing technology.

Many attempts have been made in the field of hair dyeing in order to improve the dyeing properties such as obtaining the shades of the desired intensity or obtaining wide choices of colors shades.

For example, in order to improve the process of hair dyeing and to limit the inconveniences associated with the use of alkalizing agent and oxidizing agent it is known to use in a dye composition a substantial amount of one or more fatty substances such as oils. This improves the color process for the stylist and consumer by enabling the use of alternate alkali materials to ammonia used within conventional hair colorant. For example, monoethanolamine which has no unpleasant odour may be used.

However, the introduction of a large amount of oil, in replacement of water in a dyeing formulation proves to be problematic, it may affect the range of colors that may be obtained compared to a classic hair dyeing compositions.

Fewer shades of colors can be obtained with a dyeing composition comprising a large amount of fatty substances. This does not meet with the users' needs, who expect, and want to be able to choose from a full range of colors and tones.

Thus, there is a need to have satisfactory efficacy for dyeing products, especially in terms of range of color shades delivered, while at the same time providing a pleasant usage experience.

SUMMARY OF THE INVENTION

The inventors have surprisingly found that these needs can be met by the agent for dyeing keratin fibers according to the present invention, wherein the concentration of alkalizing agent after mixture is not more than 1.75% by weight relative to the total weight of the mixture.

While a composition with a high oil concentration cannot deliver the range of colors shades needed, the agent for dyeing keratin fibers according to the present invention presents a wider range of color shades.

The present invention relates to an agent for dyeing keratin fibers, the agent comprising:
  a composition A comprising at least one alkalizing agent, at least one oxidative dye precursor, at least one surfactant and at least one fatty substance free of carboxylic acid groups, and,
  a composition B comprising at least one oxidizing agent and at least one surfactant,
  wherein the concentration of fatty substances free of carboxylic acid groups after mixing composition A and composition B is at least 20% by weight relative to the total weight of the mixed composition A and B, and
  wherein the concentration of alkalizing agent after mixing composition A and composition B is not more than 1.75% by weight relative to the total weight of the mixed composition A and B.

The agent according to the invention is particularly effective especially regarding the chromaticity of the dyeing obtained on the keratin fibers.

The present invention also relates to a process for dyeing keratin fibers, comprising the application to the wet or dry keratin fibers, successively or without intermediate rinsing, of the composition A as defined hereinbefore and the composition B as defined hereinbefore.

The present invention also relates to a process for dyeing keratin fibers, comprising the application to the wet or dry fibers of the agent obtained by extemporaneous mixing of composition A and composition B as defined hereinbefore.

The present invention also relates to a kit for dyeing keratin fibers comprising the agent for dyeing keratin fibers as defined hereinbefore, wherein a first compartment contains composition A as defined hereinbefore and a second compartment contains composition B as defined hereinbefore.

DETAILED DESCRIPTION OF THE INVENTION

Definitions

In this document, including in all embodiments of all aspects of the present invention, the following definitions apply unless specifically stated otherwise.

The term "hair" as used herein means mammalian hair including scalp hair, facial hair and body hair, more preferably hair on the human head and scalp. Hair comprises hair fibers. As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

The human keratin fibers treated via the agent according to the invention are preferably hair.

The term "comprising" means that other steps and other ingredients can be added. "Comprising" encompasses the terms "consisting of" and "consisting essentially of".

The term "derivatives" as used herein includes but is not limited to: ester, amide, carboxyl, amino, ether, acetyl, acid, their salts and/or their alcohol or hydroxy derivatives of a given compound.

The term "molecular weight of a polymer" or "M.Wt. of a polymer" as used herein refers to the weight average molecular weight unless otherwise stated. The weight average molecular weight may be measured by gel permeation chromatography.

The term "cosmetically acceptable salt" as used herein refers to conventional base-addition salts that retain the properties of the one or more acrylic compounds of the present invention and are formed from suitable organic or inorganic bases. Sample base-addition salts include those derived from sodium, potassium, ammonium, calcium, magnesium, iron, zinc, zirconium and aluminium hydroxide. Chemical modification of a compound bearing a carboxylic acid function into the corresponding carboxylate salt is a technique well known in the art.

All percentages are by total weight (w/w) of the composition, unless otherwise specified. All ratios are weight ratios. "% wt." means percentage by weight. References to 'parts' e.g. a mixture of 1 part X and 3 parts Y, is a ratio by weight.

The term "kit" as used herein means a packaging unit comprising a plurality of compartments i.e. a kit of parts. An example of a kit is, for example, a first composition and a separately packaged second composition. Another kit may comprise application instructions comprising a method and a composition/formulation.

Description of the Invention

An agent for dyeing keratin fibers comprises a composition A and a composition B. Composition A may be an inverse emulsion (water-in-oil) and composition B may be a direct emulsion (oil-in-water). It is known in the art that an emulsion comprises a dispersed phase and a continuous phase.

The composition A and the composition B may be in various forms, such as in the form of liquids, milks or crème, or in any other form that is suitable for dyeing keratin fibers, and especially human hair.

Preferably, composition A and composition B are in the form of a milk or a crème.

Composition A comprises at least one alkalizing agent, at least one oxidative dye precursor, at least one surfactant and at least one fatty substance free of carboxylic acid groups.

Composition B comprises at least one oxidizing agent and at least one surfactant.

Fatty Substances

Composition A comprises at least one fatty substance free of carboxylic acid groups.

Composition B may also comprise at least one fatty substance free of carboxylic acid groups.

The term "fatty substance" means an organic compound that is an insoluble organic in water at room temperature (25° C.) and at atmospheric pressure (760 mmHg) (solubility of less than 5%, preferably 1% and more preferably still 0.1%). In addition, under the same temperature and pressure conditions, the fatty substances are soluble in organic solvents such as chloroform, ethanol or benzene, for example.

The term "fatty substance free of carboxylic acid groups" means fatty substance containing no —COOH groups and no —COO groups.

Preferably, composition A and/or composition B comprises no fatty substances with carboxylic acid groups.

The fatty substances of the invention are not oxyalkylenated.

Preferably, the fatty substances of the invention are selected from the group of liquid hydrocarbons, non-silicone oils of animal, plant, mineral or synthetic origin, liquid fatty alcohols, liquid fatty esters, silicones and fatty ethers, or mixtures thereof.

The fatty substances of the invention may be liquid or non-liquid at room temperature (25° C.) and at atmospheric pressure (760 mmHg; i.e. $1.013 \times 10^5$ Pa). The liquid fatty substances of the invention preferably have a viscosity of less than or equal to 2 Pa·s, better less than or equal to 1 Pa·s and even better less than or equal to 0.1 Pa·s at a temperature of 25° C. and at a shear rate of 1 $s^{-1}$. The term "liquid hydrocarbon" means a hydrocarbon composed solely of carbon and hydrogen atoms, which is liquid at room temperature (25° C.) and at atmospheric pressure (760 mmHg; i.e. $1.013 \times 10^5$ Pa).

More particularly, the liquid hydrocarbons are chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane.

linear or branched hydrocarbons of mineral, animal or synthetic origin with more than 16 carbon atoms, such as volatile or non-volatile liquid paraffins and derivatives thereof, petroleum jelly, liquid petroleum jelly, polydecenes, hydrogenated polyisobutene such as Parleam®, and squalane.

Preferably, the liquid hydrocarbon(s) is (are) chosen from volatile or non-volatile liquid paraffins, and liquid petroleum jelly.

The term "liquid fatty alcohol" means a non-glycerolated and non-oxyalkylenated fatty alcohol that is liquid at room temperature (25° C.) and at atmospheric pressure (760 mmHg; i.e. $1.013 \times 10^5$ Pa).

Preferably, the liquid fatty alcohols of the invention comprise from 8 to 30 carbon atoms.

The liquid fatty alcohols of the invention may be saturated or unsaturated. The saturated liquid fatty alcohols are preferably branched. They may optionally comprise in their structure at least one aromatic or non-aromatic ring. They are preferably acyclic.

More particularly, the liquid saturated fatty alcohols of the invention are chosen from octyldodecanol, isostearyl alcohol and 2-hexyldecanol. Preferably, the liquid saturated fatty alcohol of the invention is octyldodecanol.

These liquid unsaturated fatty alcohols have at least one double or triple bond. Preferably, the fatty alcohols of the invention bear in their structure one or more double bonds. When several double bonds are present, there are preferably 2 or 3 of them, and they may be conjugated or non-conjugated. These unsaturated fatly alcohols may be linear or branched. They may optionally comprise in their structure at least one aromatic or non-aromatic ring. They are preferably acyclic.

More particularly, the liquid unsaturated fatty alcohols of the invention are chosen from oleyl alcohol, linoleyl alcohol, linolenyl alcohol and undecylenyl alcohol.

The term "liquid fatty ester" means an ester derived from a fatty acid and/or from a fatty alcohol and that is liquid at room temperature (25° C.) and at atmospheric pressure (760 mmHg; i.e. $1.013 \times 10^5$ Pa).

The esters are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, there are ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{25}$ dihydroxy, trihydroxy, tetrahydroxy or pentahydroxy alcohols may also be used.

There are also diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

The composition A and/or the composition B may also comprise, as liquid fatty ester, sugar esters and diesters of $C_6$-$C_{30}$ and preferably $C_{12}$-$C_{22}$ fatty acids. The term "sugar" means oxygen-bearing hydrocarbon-based compounds which contain several alcohol functions, with or without aldehyde or ketone functions, and which comprise at least 4 carbon atoms. These sugars may be monosaccharides, oligosaccharides or polysaccharides.

Examples of suitable sugars include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

Monoesters and diesters and especially sucrose, glucose or methylglucose monooleates or dioleates, stearates, behenates, oleopalmitates, linoleates, linolenates and oleostearates are more particularly used.

Finally, natural or synthetic esters of monoacids, diacids or triacids with glycerol may also be used.

Among these are plant oils. As oils of plant origin or synthetic triglycerides that may be used in the composition of the invention as liquid fatty esters, examples that may be mentioned include:
  triglyceride oils of plant or synthetic origin, such as liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, jojoba oil and shea butter oil.

The term "liquid silicone" means an organopolysiloxane that is liquid at ordinary temperature (25° C.) and at atmospheric pressure (760 mmHg; i.e. $1.013 \times 10^5$ Pa).

Preferably, the silicone is chosen from liquid polydialkylsiloxanes, especially liquid polydimethylsiloxanes (PDMSs) and liquid polyorganosiloxanes comprising at least one aryl group.

These silicones may also be organomodified. The organomodified silicones that can be used are liquid silicones as defined above and comprising in their structure one or more organofunctional groups attached via a hydrocarbon-based group. They may be volatile or non-volatile. When they are volatile, the silicones are more particularly chosen from those having a boiling point of between 60° C. and 260° C., and more particularly still from:
  (i) cyclic polydialkylsiloxanes comprising from 3 to 7 and preferably 4 to 5 silicon atoms;
  (ii) linear volatile polydialkylsiloxanes containing 2 to 9 silicon atoms and having a viscosity of less than or equal to $5 \times 10^{-6}$ m$^2$/s at 25° C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups. There is also polydimethylsiloxanes containing dimethylsilanol end groups known under the name Dimethiconol (CTFA).

The organomodified liquid silicones may especially contain polyethyleneoxy and/or polypropyleneoxy groups.

Composition A and/or composition B may also comprise non-liquid fatty substance at room temperature and at atmospheric pressure.

The term "non-liquid" preferably means a solid compound or a compound that has a viscosity of greater than 2 Pa·s at a room temperature of 25° C. and at a shear rate of 1 s$^{-1}$.

More particularly, the non-liquid fatty substances are chosen from fatty alcohols, esters of fatty acids and/or of fatty alcohols, non-silicone waxes, silicones and fatty ethers, which are non-liquid and preferably solid.

The non-liquid fatty alcohols may be chosen from saturated or unsaturated, linear or branched alcohols comprising from 8 to 30 carbon atoms, for example, of cetyl alcohol, stearyl alcohol and a mixture thereof (cetylstearyl alcohol).

Preferably, the non-liquid fatty alcohol of the invention is cetylstearyl alcohol.

As regards the non-liquid esters of fatty acids and/or of fatty alcohols, there are especially solid esters derived from $C_9$-$C_{26}$ fatty acids and from $C_9$-$C_{26}$ fatty alcohols. Among these esters, mention may be made of octyldodecyl behenate; isocetyl behenate; cetyl lactate; stearyl octanoate; octyl octanoate; cetyl octanoate; decyl oleate; myristyl stearate; octyl palmitate; octyl pelargonate; octyl stearate; alkyl myristates such as cetyl, myristyl or stearyl myristate; hexyl stearate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

There is also diethyl sebacate: diisopropyl sebacate; diisopropyl adipate; di-n-propyl adipate; dioctyl adipate; dioctyl maleate.

Among all the additional esters mentioned above, it is preferred to use myristyl, cetyl or stearyl palmitates, alkyl myristates such as cetyl myristate, and stearyl myristyl myristate.

The (non-silicone) wax(es) may be selected from carnauba wax, candelilla wax, esparto grass wax, paraffin wax, ozokerite, plant waxes such as olive wax, rice wax, hydrogenated jojoba wax or the absolute waxes of flowers, animal waxes, for instance beeswaxes or modified beeswaxes (cerabellina).

Composition A and/or composition B may comprise non-liquid silicones in the form of waxes, resins or gums.

The non-liquid silicone may be chosen from polydialkylsiloxanes, especially polydimethylsiloxanes (PDMSs), and organomodified polysiloxanes comprising at least one functional group chosen from poly(oxyalkylene) groups, amino groups and alkoxy groups.

The silicone gums are especially polydialkylsiloxanes and preferably polydimethylsiloxanes with high number-average molecular weights of between 200000 and 1000000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane or mixtures thereof.

The non-liquid fatty ethers may be chosen from dialkyl ethers and especially dicetyl ether and distearyl ether, alone or as a mixture.

Preferably, the fatty substance use in composition A and/or composition B do not comprise any oxyalkylene units or any glycerol units.

Preferably, the fatty substances free of carboxylic acid groups used in composition A and/or in composition B, which may be identical or different, are selected from the group of liquid paraffins, liquid petroleum jelly, polydecenes, liquid fatty acid esters, liquid fatty alcohols such as octyldodecanol or non-liquid fatty alcohols such as cetylstearyl alcohol, and mixtures thereof.

More preferably, the fatty substances free of carboxylic acid groups are selected from the group of liquid petroleum jelly, liquid fatty alcohols such as octyldodecanol or non-liquid fatty alcohols such as cetylstearyl alcohol, and mixtures thereof.

Preferably, the composition A and/or composition B of the invention contain one or more fatty substances that are liquid at room temperature (25° C.) and at atmospheric pressure (760 mmHg; i.e. $1.013 \times 10^5$ Pa), optionally combined with one or more fatty substances that are non-liquid under the same conditions.

Composition A comprises an amount of fatty substances free of carboxylic acid groups of greater than 25%, preferably greater than 30%, more preferably greater than 40%, even more preferably greater than 50% by total weight of composition A.

Composition B comprises an amount of fatty substances free of carboxylic acid groups of greater than 10%, preferably greater than 15%, but not more than 40% by total weight of composition B.

Preferably, the concentration of fatty substances free of carboxylic acid groups ranges from 25% to 80%, more preferably from 30% to 70% by total weight of concentration A.

The total amount of fatty substances free of carboxylic acid groups after mixing composition A and composition B represents at least 20%, preferably at least 25%, more preferably at least 30% by total weight of the mixed composition A and B.

The total amount of fatty substances free of carboxylic acid groups after mixing composition A and B is from 25% to 70% and more preferably from 30% to 60% by total weight of the mixed composition A and B.

Alkalizing Agents

Composition A according to the present invention comprises at least one alkalizing agents.

By "alkalising agent", it is meant one or more compounds suitable for increasing the pH to alkaline level. That is to say, the alkalising agent(s) is (are) generally such that the $pK_b$ at 25° C. is less than 12, preferably less than 10 and more advantageously less than 6. Generally, the most commonly used alkalising agent in the art is ammonia. Non-ammonia alkalising agents are also known and advantageous in view of reduced olfactory stimulation, e.g. alkanolamines.

Suitable alkalizing agents include, but are not limited to: ammonia; alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal and ammonium hydroxides (such as sodium hydroxide); alkali metal and ammonium carbonates; and mixtures thereof. Typical alkalizing agents are ammonia and/or monoethanolamine.

The composition (A) may comprise one or more non-ammonia alkalizing agents selected from the group consisting of: monoethanolamine (MEA), sodium silicate, sodium meta silicate, diethanolamine, triethanolamine, monopropanolamine, dipropanolamine, tripropanolamine, 2-amino-2-methyl-1,3-propanediol, 2-amino-2-methyl-1-propanol (a.k.a. aminomethylpropanol, AMP), 2-amino-2-hydroxymethyl-1,3-propanediol, and mixtures thereof.

Monoethanolamine (MEA) or aminomethylpropanol (AMP) are commonly used in ammonia-free hair dye products.

Preferably, the alkalising agent is monoethanolamine (MEA) or aminomethylpropanol (AMP) alone or in combination with each other or other alkalizing agents. More preferably, the alkalising agent is monoethanolamine.

Monoethanolamine may in particular be preferred to be used alone or in combination with other non-ammonia alkalising agent.

The composition A according to the invention preferably does not comprise any aqueous ammonia or salts thereof as alkalising agent. If however, it did comprise any, its content would not exceed 0.03% by weight, preferably not exceed 0.01% by total weight of the composition A.

Preferably, if the composition A comprises aqueous ammonia or a salt thereof, then the amount of non-ammonia alkalising agent is greater than the amount of aqueous ammonia.

The composition may comprise an alkalising agent which is monoethanolamine (MEA) and a primary intermediate which is 2-methoxymethyl-1,4-benzenediamine.

Composition A may comprise a total amount of alkalizing agent ranging from 0.1% to 3.5% by weight, preferably from 0.5% to 3.25% by weight, more preferably from 1.0% to 3.25% by weight relative to the total weight of the composition A.

Composition A may comprise a total amount of alkalizing agent of less than 3.5% by weight, preferably less than 3.4% by weight, more preferably less than 3.3% by weight relative to the total weight of the composition A.

The concentration of alkalizing agent after mixing composition A and composition B is not more than 1.75% by weight relative to the total weight of the mixed composition A and B.

Preferably, the concentration of alkalizing agent after mixing composition A and composition B is from 0.5% to 1.70% by weight, more preferably from 1.0% to 1.65% by weight relative to the total weight of the mixed composition A and B.

Oxidative Dye/Direct Dye

The composition A of the invention comprises at least one oxidative dye precursor.

Composition A may comprise at least one oxidative dye precursor, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Preferably, the composition A comprises oxidative dye precursors comprising one or more couplers and one or more primary intermediates.

The oxidative dye precursors suitable for use herein, in so far as they are bases, may be used as free bases or in the form of any cosmetically acceptable salts obtained with the corresponding organic or inorganic acids, such as hydrochloric, hydrobromic, citric, acetic, lactic, succinic, tartaric, or sulfuric acids, or, in so far as they have aromatic hydroxyl groups, in the form of any cosmetically acceptable salts obtained with the corresponding bases, such as alkali phenolates.

Oxidative dye precursors are known in the art, and include aromatic diamines, aminophenols, aromatic diols and their derivatives (a representative but not exhaustive list of oxidation dye precursors can be found in Sagarin, "Cosmetic Science and Technology", Interscience, Special Edn. Vol. 2 pages 308 to 310). Suitable oxidative dye precursors are also disclosed in the Canadian Patent Application No. CA2576189A1—in particular, from Table 1 dye combinations No. 1 to 2394, which span pages 49 to 238, are incorporated herein by reference. It is to be understood that the one or more primary intermediates and the one or more couplers (collectively known as oxidative dye precursors) detailed below are only by way of example and are not intended to limit the compositions and other aspects herein described. The one or more primary intermediates and the one or more couplers may be used in the form of any cosmetically acceptable salts, for example sulfate salts.

Typically, the composition A may comprise a total amount of oxidative dye precursors ranging up to 12%, from 0.001% to 12%, preferably from 0.1% to 10%, more preferably from 0.3% to 8%, even more preferably from 0.3% to 6%, by total weight of the composition A.

The one or more primary intermediates may be selected from the group consisting of toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino) phenol, 4-amino-m-cresol, 6-amino-m-cresol, 5-ethyl-o-aminophenol, 2-methoxy-p-phenylenediamine, 2,2'-metylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, their salts thereof and mixtures thereof.

The one or more primary intermediate of the composition may be particularly 1,4-diamino-2-(methoxymethyl)-benzene. 1,4-diamino-2-(methoxymethyl)-benzene has the advantage of an improved sensitisation profile (i.e. reduced risks of scalp skin reaction).

The one or more primary intermediate may be 4,5-diamino-1-hexylpyrazole. 4,5-diamino-1-hexylpyrazole may be used as a sulfate salt.

The one or more primary intermediate may be selected from the group consisting of 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, and mixtures thereof; and the cosmetically acceptable salts thereof such as chlorides, sulfates and hemi-sulfates in particular.

The one or more couplers may be a compound comprising one or more phenyl rings substituted with one or more hydroxyl groups.

The one or more couplers may be selected from the group consisting of resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene) bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5- naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyrimidine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The oxidative dye precursors may be particularly selected from the group consisting of 1-naphthol, 2,4-diaminophenoxyethanol, toluene-2,5-diamine sulfate, resorcinol, 4-amino-m-cresol, 2-amino-4-hydroxyethylaminoanisole sulfate, hydroxyethyl-3,4-methylenedioxyaniline HCl, 1-hydroxyethyl 4,5-diamino pyrazole sulfate, 4-amino-2-hydroxytoluene, 2-methylresorcinol, m-aminophenol, 2-methyl-5-hydroxyethylaminophenol, and mixtures thereof.

Preferably, the oxidative dye precursor comprises at least one primary intermediate selected from the group consisting of toluene-2,5-diamine, 2-methoxymethyl-p-phenylenediamine, N,N-bis(2-hydroxyethyl)-p-phenylenediamine, p-aminophenol and mixtures thereof, and at least one coupler selected from the group consisting of resorcinol, methyl-resorcinol, naphthol, m-aminophenol and mixtures thereof.

The composition A according to the present invention may further comprise compatible direct dyes, in an amount sufficient to provide additional colouring, particularly with regard to intensity. The composition may further comprise one or more direct dyes, advantageously one or more oxidatively stable direct dyes.

Typically, composition A may comprise a total amount of direct dyes ranging from 0.001% to 4%, preferably from 0.005% to 3%, more preferably from 0.01% to 2%, by total weight of the composition A.

The presence of one or more direct dyes and the proportion thereof can help to provide or enhance dyeing, particularly with regard to the vibrancy of the color that is desired.

Preferably, composition A is substantially free of any direct dyes.

The one or more direct dyes may be selected from the group consisting of nitro dyes to provide a blue color, nitro dyes to provide either a red color or a yellow color, quinone dyes, basic dyes, neutral azo dyes, acid dyes, and mixtures thereof. The one or more direct dyes may be a basic dye. The one or more direct dyes may be a neutral azo dye. The one or more direct dyes may be an acid dye.

The one or more direct dyes may be selected from the group consisting of Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, 2-amino-6-chloro-4-nitrophenol, (E)-4-(4-(2-methyl-2-phenylhydrazono)methyl)pyridimum-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

Surfactants

Composition A comprises at least one surfactant.

Composition B comprises at least one surfactant.

A surfactant can help to provide an emulsion.

Composition A may comprise from 0.001% to 30%, preferably from 0.1% to 25%, more preferably from 0.2% to 20%, even more preferably from 0.4% to 15%, of surfactants by total weight of composition A.

Composition B may comprise from 0.001% to 10%, preferably from 0.01% to 8%, more preferably from 0.01% to 7%, even more preferably from 0.05% to 5%, even much more preferably from 0.1% to 5%, of surfactants by total weight of composition B.

Preferably, composition A and/or composition B comprise one or more surfactants selected from the group consisting of anionic surfactants, non-ionic surfactants, amphoteric surfactants, zwitterionic surfactants, cationic surfactants, and mixtures thereof.

The one or more surfactants of the composition can be useful for stabilising a hydrophobic phase in the composition, e.g. for stabilising the gel network and/or lamellar structure.

Composition A and/or composition B may comprise an anionic surfactant. The anionic surfactants may be selected from the group consisting of salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Suitable anionic surfactant(s) may comprise at least one anionic functional groups at their head selected from sulfate, sulfonate, phosphate and carboxylates.

Suitable alkyl sulfates include ammonium lauryl sulfate, sodium lauryl sulfate (sodium dodecyl sulfate, SLS, or SDS), and alkyl-ether sulfates, such as sodium laureth sulfate (sodium lauryl ether sulfate or SLES), and sodium myreth sulfate.

Further suitable anionic surfactants may include Docusate (dioctyl sodium sulfosuccinate), alkyl-aryl ether phosphate, alkyl ether phosphate, alkyl carboxylate, such as sodium stearate, sodium lauroyl sarcosinate, ammonium laureth sulfate, disodium lauryl sulfosuccinate, and sodium lauryl sulphoacetate.

Preferred anionic surfactants may be selected from the group consisting of sodium laurylethersulfate, sodium laurethethersulfate, sodium dodecyl sulfate, ammonium laurethethersulfat, ammonium dodecyl sulfate, alkylbenzenesulfonate, and combinations thereof.

The one or more surfactants of composition A and/or composition B may be non-ionic surfactants. The non-ionic surfactant(s) may be selected from the group consisting of lanolin alcohol, and polyoxyethylene ethers of fatty alcohols, and mixtures thereof. The non-ionic surfactant may be preferably ceteareth-n, wherein n is from 2 to 100, or from 10 to 30. When the one or more surfactants of the composition are non-ionic, precipitation of others ingredients of the composition can be prevented. Suitable nonionic surfactants are compounds that are well known (see, for example, in this respect "Handbook of Surfactants" by M. R. Porter, published by Blackie & Son (Glasgow and London), 1991, pp. 116-178).

The nonionic surfactants are more particularly chosen from monooxyalkylenated or polyoxyalkylenated, monoglycerolated or polyglycerolated nonionic surfactants. The oxyalkylene units are more particularly oxyethylene or oxypropylene units, or a combination thereof, such as POE/POP/PGE (INCI: Poloxamer 184) (trade name: Pluracare L64, BASF), preferably oxyethylene units.

Examples of oxyalkylenated nonionic surfactants that may be mentioned include:
oxyalkylenated ($C_8$-$C_{24}$)alkylphenols,
saturated or unsaturated, linear or branched, oxyalkylenated $C_8$-$C_{30}$ alcohols such as oxyethylenated cetylstearyl alcohol (33OE) or oleyl alcohol (10OE),
saturated or unsaturated, linear or branched, oxyalkylenated $C_8$-$C_{30}$ amides,
esters of saturated or unsaturated, linear or branched, $C_8$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils,
condensates of ethylene oxide and/or of propylene oxide, and mixtures thereof.

These surfactants contain a number of moles of ethylene oxide and/or of propylene oxide of between 1 and 100 and preferably between 2 and 50. Advantageously, the nonionic surfactants do not comprise any oxypropylene units.

Preferably, the oxyalkylenated nonionic surfactants are chosen from oxyethylenated $C_8$-$C_{30}$ alcohols, and esters of $C_8$-$C_{30}$ acids and of polyethylene glycols.

As examples of monoglycerolated or polyglycerolated nonionic surfactants, monoglycerolated or polyglycerolated $C_8$-$C_{40}$ alcohols are preferably used. In particular, the monoglycerolated or polyglycerolated $C_8$-$C_{40}$ alcohols correspond to the following formula:

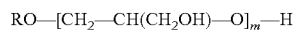

$$RO—[CH_2—CH(CH_2OH)—O]_m—H$$

in which R represents a linear or branched $C_8$-$C_{40}$ and preferably $C_8$-$C_{30}$ alkyl or alkenyl radical, and m represents a number ranging from 1 to 30 and preferably from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

Among the monoglycerolated or polyglycerolated alcohols, it is more particularly preferred to use the $C_8$-$C_{10}$ alcohol containing 1 mol of glycerol, the $C_{10}$-$C_{12}$ alcohol containing 1 mol of glycerol and the $C_{12}$ alcohol containing 1.5 mol of glycerol.

Preferably, the non-ionic surfactants of composition A and/or composition B are selected from the group consisting of POE/POP/POE (Poloxamer 184), oxyethylenated $C_8$-$C_{30}$ alcohols such as oxyethylenated cetylstearyl alcohol (33OE) or oleyl alcohol (10OE), esters of $C_8$-$C_{30}$ acids and of polyethylene glycols and mixtures thereof.

More preferably, the non-ionic surfactants of composition A and/or composition B are selected from the group consisting of POE/POP/POE (Poloxamer 384), oxyethylenated $C_8$-$C_{30}$ alcohols, such as oxyethylenated cetylstearyl alcohol (33OE) or oleyl alcohol (10OE) and mixtures thereof.

Preferably, the surfactants of composition A and/or composition B are non-ionic surfactants.

Preferably, the composition B comprises at least one nonionic surfactant selected from the group consisting of oxyethylenated $C_8$-$C_{30}$ alcohols such as oxyethylenated cetylstearyl alcohol (33OE) and mixtures thereof.

Preferably, the composition A comprises at least one nonionic surfactant selected from the group consisting of POE/POP/POE (Poloxamer 184) or oxyethylenated $C_8$-$C_{30}$ alcohols such as oleyl alcohol (10OE) and mixtures thereof.

The total amount of surfactants after the mixture of composition A and composition B is from 0.1% to 20%, alternatively from 0.1% to 15%, alternatively from 0.2% to 10% by total weight of the mixture of composition A and composition B.

Thickeners

Composition A and/or composition B may also comprise one or more thickeners.

These thickeners may be chosen from fatty acid amides (coconut acid diethanolamide or monoethanolamide, oxyethylenated alkyl ether carboxylic acid monoethanolamide), polymeric thickeners such as cellulose-based thickeners (hydroxyethyl cellulose, hydroxypropylcellulose, carboxymethylcellulose), guar gum and derivatives thereof (hydroxypropylguar), fumed silicas, and clays, especially bentonites and hectorites, and derivatives thereof.

The content of thickener(s), if they are present, usually ranges from 0.01% to 20% and preferably from 0.1% to 5% by total weight of each of the composition A or composition B.

The clay may be organically modified clay mineral. The organically modified clay mineral is used as an emulsion aid. The organically modified clay mineral is a type of colloidal aluminum silicate hydrate that has a three-layer structure that is prepared by modifying a clay mineral with a quaternary ammonium salt cationic surfactant. For example, organically modified bentonite and organically modified hectorite can be used.

Specific examples include dimethyldistearyl ammonium hectorite, dimethyl alkyl ammonium hectorite, benzyl dimethyl stearyl ammonium hectorite, and aluminum magnesium silicate treated with distearyl dimethyl ammonium chloride.

Preferably, the thickeners are clays such as dimethyldistearyl ammonium hectorite.

Preferably, the thickener used in composition A and/or composition B is dimethyldistearyl ammonium hectorite.

Chelants

Composition A and/or composition B may further comprise one or more chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, composition A and/or composition B may comprise each a total amount of chelants ranging from at least 0.01%, preferably from 0.01% to 5%, more preferably from 0.25% to 3%, even more preferably from 0.5% to 2%, by total weight of each of the composition A or composition B.

The one or more chelants may be selected from the group consisting of carboxylic acids (such as aminocarboxylic acids), phosphonic acids (such as aminophosphonic acids), polyphosphoric acids (such as linear polyphosphoric acids), their salts thereof, and mixtures thereof.

By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, calcium salts, magnesium salts, ammonium salts, and mixtures thereof; alternatively monoethanolammonium salts, diethanolammonium salts, triethanolammonium salts, and mixtures thereof.

The one or more chelants may be one or more aminocarboxylic acid chelants comprising one or more carboxylic acid moieties (—COOH) and one or more nitrogen atoms. The one or more aminocarboxylic acid chelants may be selected from the group consisting of diethylenetriamine pentaacetic acid (DTPA), diethylenetriamine-N,N',N''-polyacids, ethylenediamine disuccinic acid (EDDS), ethylenediamine-N,N'-diglutaric acid (EDDG), 2-hydroxypropylenediamine-N—N'-disuccinic acid (HPDDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis (2-hydroxybenzyl)ethylenediamine-N,N'-diacetic acid (HBED), ethylene diamine tri(methylene phosphonate), hexamethylene diamine tetra (methylene phosphonate), their salts thereof, and mixtures thereof.

Alternatively, the one or more aminocarboxylic acid chelants may be selected from the group consisting of iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, dipicolinic acid, 2-phosphonobutane-1,2,4-tricarboxylic acid, their salts thereof, their derivatives thereof, and mixtures thereof.

The one or more chelants may be one or more aminophosphonic acid chelants comprising an aminophosphonic acid moiety (—PO$_3$H$_2$) or its derivative —PO$_3$R$_2$, wherein R$_2$ is a C$_1$ to C$_6$ alkyl or aryl radical and salts thereof.

The one or more aminophosphonic acid chelants may be selected from the group consisting of aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

Other various chelants may also be contemplated, including the amino phosphonates, available as Dequest™ from Monsanto, the nitriloacetates, the hydroxyethyl-ethylene triamines and the like which are known for such use. Suitable chelants for use herein may include organic phosphonates, such as the amino alkylene poly (alkylene phosphonates), alkali metal ethane 1-hydroxy disphosphonates and nitrilo trimethylene phosphonates.

Preferably, composition A and/or composition B comprises a chelant, which may be identical or different, selected from the group consisting of diethylenetriamine-N,N',N''-polyacids, diethylenetriaminepentaacetic acid (DTPA), diethylenetriaminepenta(methylene phosphonic acid) (DTPMP), ethylene diamine tri(methylene phosphonate), hexamethylene diamine tetra (methylene phosphonate), ethylenediaminedisuccinic acid (EDDS), their salts thereof, their derivatives thereof, and mixtures thereof.

Organic Solvents

Composition A and/or composition B may further comprise one or more organic solvents.

The one or more organic solvents may be selected to dissolve the compounds that would not typically be sufficiently soluble in water.

Suitable organic solvents include, but are not limited to: $C_1$ to $C_4$ lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglycol, polygylcerol); propylene carbonate; and mixtures thereof.

Preferably, the one or more solvents are selected from the group consisting of ethanol, propanol, isopropanol, glycerol, propylene glycol, hexylene glycol, dipropyleneglycol, propylene carbonate, and mixtures thereof.

Composition A may comprise a total amount of organic solvents ranging from 1% to 40% by weight, preferably from 5% to 30% by weight relative to the total weight of composition A.

Composition B may comprise a total amount of organic solvents ranging from 0.2% to 40% by weight, preferably from 0.5% to 30% by weight relative to the total weight of composition B.

Water

Composition A may comprise an amount of water greater than 2% by weight, preferably greater than 5% by weight relative to the total weight of composition A.

Composition A may comprise less than 50% by weight of water, preferably less than 25% by weight of water, preferably from 5% to 25% by weight of water relative to the total weight of composition A.

Composition B may comprise an amount of water greater than 10% by weight, preferably greater than 15% by weight relative to the total weight of composition B.

Composition B may comprise less than 80% by weight of water, preferably less than 70% by weight of water, preferably from 10% to 70% by weight of water relative to the total weight of composition B.

Oxidizing Agent(s)

Composition B comprises at least one oxidizing agent.

As used herein, "water-soluble" means that in standard conditions at least 0.1 g, preferably 1 g, more preferably 10 g of the oxidizing agent can be dissolved in 1 litre of deionized water at 25° C. Suitable water-soluble oxidizing agents include, but are not limited to: inorganic peroxygen materials capable of yielding hydrogen peroxide in an aqueous solution.

The one or more oxidizing agents are valuable for the initial solubilisation and decolorisation of the melanin (bleaching) and accelerate the oxidation of the oxidative dye precursors (oxidative dyeing) in the hair shaft.

Suitable water-soluble peroxygen oxidizing agents include, but are not limited to: hydrogen peroxide; inorganic alkali metal peroxides (such as sodium periodate and sodium peroxide); alkali metal bromates or ferricyanides, organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used.

The percarbonates may be used to provide a source of both oxidizing agent and carbonate ions and or ammonium ions.

The oxidizing agent(s) may preferably be selected from the group consisting of hydrogen peroxide, urea peroxide and their salts thereof, and inorganic perhydrate salts, for instance alkali metals or alkaline-earth metals salts, such as sodium, potassium or magnesium, of persulfates, perborates and percarbonates, and mixtures thereof.

More preferably, composition B comprises an oxidizing agent selected from the group consisting of hydrogen peroxide, percarbonates, persulphates, and mixtures thereof.

The particularly preferred oxidizing agent is hydrogen peroxide.

The lower limit for the oxidizing agents may be at least 0.01% by total weight of the composition B.

Composition B may comprise a total amount of oxidizing agents ranging from 0.01% to 15%, alternatively from 0.1% to 15%, alternatively from 0.2% to 15%, alternatively ranging from 0.3% to 13%, alternatively from 0.3% to 12% by total weight of composition B.

Alternatively, composition B may comprise a total amount of oxidizing agents of less than 20%, alternatively less than 18%, alternatively less than 15%, alternatively less than 13% by total weight of composition B.

The total amount of oxidizing agents after mixing composition A and composition B is from 0.1% to 10%, alternatively from 0.2% to 9%, alternatively from 0.2% to 8%, alternatively from 0.2% to 7%, alternatively from 0.2% to 6% by total weight of the mixed composition A and B.

pH Modifiers

Composition A and/or composition B may further comprise a pH modifier in an amount that is sufficiently effective to adjust the pH of the composition to fall within a range prescribed above.

Suitable pH modifiers and/or buffering agents for use herein may include, but are not limited to ammonia, acidulents (such as inorganic and inorganic acids including for example phosphoric acid, acetic acid, ascorbic acid, citric acid or tartaric acid, hydrochloric acid); alkanolamines (such as monoethanolamine, diethanolamine, triethanolamine, monopropanolamine, dipropanolamine, tripropanolamine, 2-amino-2-methyl-1-propanol, and 2-amino-2-hydroxymethyl-1,3,-propanediol); guanidium salts, alkali metal such as sodium hydroxide, tetrasodium pyrophosphate or ammonium hydroxides and carbonates; and mixtures thereof.

Composition A may have a pH from 3 to 12.

The pH of composition A may be preferably from 8.0 to 12.0, more preferably from 9.0 to 11.0.

Composition B may have a pH of less than 7.

Conditioning Agents

Composition A and/or composition B may further comprise at least one conditioning agent.

Typically, composition A may comprise a total amount of conditioning agents ranging from 0.05% to 20%, preferably from 0.1% to 15%, more preferably from 0.1% to 10% by total weight of composition A.

Similarly, composition B may comprise a total amount of conditioning agents ranging from 0.05% to 20%, preferably from 0.1% to 15%, more preferably from 0.1% to 10% by total weight of composition B.

Suitable conditioning agents include, but are not limited to: silicones, aminosilicones, fatty alcohols, polymeric resins, polyol carboxylic acid esters, cationic polymers, cationic surfactants, insoluble oils and oil derived materials, mineral oils and other oils such as glycerin and sorbitol and mixtures thereof.

The cationic polymers may be preferably selected from polymers of polyamine, polyamino amide and polyquaternary ammonium type, such as cyclopolymers of dialkdiallylamine or of dialkyldiallyammonium, including: dimethyldiallyammonium chloride polymers, such as polymers known as Polyquaternium-6.

Preferably, the conditioning agent is a cationic polymer selected from the group of cyclopolymers of dialkyldiallyamine or of dialkyldiallyammonium, such as dimethyldiallyammonium chloride polymers.

Other Ingredients

Composition A and/or composition B may comprise, in addition to the ingredients indicated above, further ingredients in order to further enhance the properties of the composition, as long as these are not excluded by the claims.

Suitable further ingredients include, but not limited to: anionic, cationic, nonionic, amphoteric or zwitterionic polymers or mixtures thereof, antioxidants, pigment, penetrating agents, sequestrants, perfumes, dispersing agents, film-forming agents, cosmetically acceptable carrier, radical scavengers, ceramides, preservatives, opacifying agents and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed herein below, whose disclosure is of course non-exhaustive.

Method and Kits

A subject of the present invention is also a process for dyeing keratin fibers, comprising the application to the said keratin fibers of the agent as described above.

According to the invention, the agent applied to keratin fibers results from the mixing of composition A and composition B, this mixing being performed either before application to keratin fibers or directly on the keratin fibers (successive application to the keratin fibers of composition A and of composition B without intermediate rinsing).

Thus, the composition A and composition B may be applied to the wet or dry keratin fibers, successively and without intermediate rinsing.

Alternatively, the agent applied to keratin fibers resulting from the mixing of composition A and composition B, may be applied to the wet or dry keratin fibers, successively and without intermediate rinsing.

In this case, the interval between the mixing of composition A and of composition B and the application of the mixed composition A and B to the hair preferably does not exceed 30 minutes, preferably 10 minutes and even more preferably five minutes.

The weight ratio of the amount of composition A used to the amount of composition B may range from 0.2 to 3 and preferably from 0.3 to 1.

In addition, the mixed composition A and B present on the keratin fibers (resulting either from the extemporaneous mixing of the composition A and of composition B or from the successive application thereof) is left on for a time generally from about 2 to about 60 minutes, typically about 30 to about 45 minutes.

The temperature during the process is, conventionally, preferably between room temperature (between 15 and 25° C.) and 80° C. and preferably between room temperature and 60° C.

After the treatment, the keratin fibers are optionally rinsed with water, optionally undergo washing with a shampoo followed by rinsing with water, and are then dried or left to dry.

Another subject of the present invention is a kit for dyeing keratin fibers, comprising the agent for dyeing keratin fibers as defined hereinbefore, wherein a first compartment contains composition A as defined hereinbefore and a second compartment contains composition B as defined hereinbefore.

Retail oxidative hair dye compositions are usually sold in kits comprising, in individually packaged components such as separate containers, a dye component (also called "dye cream" for emulsions or "dye liquid" for solutions) comprising the oxidative dye precursors and alkalizing agent in a suitable carrier and; a oxidizing component (also called "hydrogen peroxide cream" for emulsions or "hydrogen peroxide liquid" for solutions) comprising the oxidizing agent (usually hydrogen peroxide). The consumer mixes the dye component, i.e composition A and oxidizing component, i.e. composition B together immediately before use and applies it onto the hair. For the professional hair salon market, the hair dye component and the oxidizing component are typically supplied independently to allow the professional to select a preferred combination.

After working the combined mixture for a few minutes (to insure uniform application to all of the hair), the dye composition is allowed to remain on the hair for an amount sufficient for the dyeing to take place (usually from about 2 to about 60 minutes, typically about 30 to about 45 minutes). The consumer or salon professional then rinses the hair thoroughly with water and/or shampoo and allows it to dry. It will be observed that the hair has changed from its original colour to the desired colour.

In both retail and professional applications, an optional conditioning agent can also be provided. In this embodiment, all three compositions can be mixed immediately before use and applied together, or the conditioning agent can be applied (after an optional rinse step), as a post-treatment immediately after the dye composition resulting from the mixture of the other containers.

The kits may also comprise as optional components a pre-treatment composition and/or a colour refresher composition. Such colour refresher compositions comprise at least one pre-formed dye and may be applied to the hair after the oxidative colour i.e. from about 1 minute after oxidative hair dye application to about 60 days after the application. These colour refresher composition can be used to increase the initial colour obtained and/or boost the colour during the wash and style cycle until the next oxidative colouring event.

EXAMPLES

The following are non-limiting examples of the agent of the present invention. The examples are given solely for the purpose of illustration and are not to be construed as limitations of the present invention, as many variations thereof are possible without departing from the spirit and scope of the invention, which would be recognized by one of ordinary skill in the art.

The commercial names of the compounds presented in example 1 also apply for examples 2 and 3.

QS" or "QSP" means sufficient quantity for 100% or for 100 g.

Example 1

The following dyeing composition is prepared (in the table below, the amounts are expressed in grams). The dye composition corresponds to compositions A1 to A3.

|  | Composition A1 Amount (% w/w) | Composition A2 Amount (% w/w) | Composition A3 Amount (% w/w) |
|---|---|---|---|
| Liquid petroleum jelly (Marcol 52, EXXON) | 55 | 55 | 55 |
| Octyldodecanol (Eutanol G, BASF) | 10 | 10 | 10 |
| Oleyl alcohol (10 OE) (Oleth-10, CRODA) | 5 | 5 | 5 |
| Distearyldimethylammonium-modified hectorite (FRGEL200, HANGZHOU SINO-HOLDING CHEMICALS CO., LTD) | 1.5 | 1.5 | 1.5 |
| Toluene-2,5-diamine sulfate | 0.55 | 0.55 | 0.55 |
| Naphthol | 1.8 | 1.8 | 1.8 |
| Ascorbic acid (OSKAR BERG GMBH) | 0.25 | 0.25 | 0.25 |
| Propylene carbonate (SIGMA ALDRICH) | 0.5 | 0.5 | 0.5 |
| Propylene glycol (BASF) | 2 | 2 | 2 |
| Ethanol (KWST) | 2.5 | 2.5 | 2.5 |
| Monoethanolamine (SASOL) | 4.5 | 3.25 | 2.0 |
| Hexylene glycol (UNIVAR) | 1 | 1 | 1 |
| Dipropylene glycol (DOW) | 1 | 1 | 1 |
| POE/POP/POE (Poloxamer 184) (Pluracare L64, BASF) | 9 | 9 | 9 |
| Diethylenetriaminepentaacetic acid (Diethylenetriamine-pentaacetic acid pentasodium salt solution, purum, 40% in H2O, SIGMA ALDRICH) | 1 | 1 | 1 |
| Sodium hydroxide | 0.4 | 0.4 | 0.4 |
| Demineralized water | Qs 100 | Qs 100 | Qs 100 |

Different amounts of alkalinizing agent, which is monoethanolamine, are tested in compositions A1 to A3.

The oxidizing composition corresponds to composition B in accordance with the present invention.

| Composition B | Amount (% w/w) |
|---|---|
| Liquid petroleum jelly (Marcol 52, EXXON) | 20 |
| Cetearyl alcohol (BASF) | 8 |
| Oxyethylenated cetylstearyl alcohol (33 OE) (Simulsol CS Ecailles Cetareth-33, SEPPIC) | 3 |
| Glycerol (SIGMA ALDRICH) | 0.5 |
| Hydrogen peroxide (50% Hydroxide peroxide Interox co-50, SOLVAY) | 12 |
| Sodium stannate (Sodium stannate trihydrate, 95%, SIGMA ALDRICH) | 0.04 |
| Tetrasodium pyrophosphate (Sodium pyrophosphate tetrabasic decahydrate, ACS reagent, ≥99%, SIGMA ALDRICH) | 0.03 |
| Polyquaternium-6 (40% Solution, Matrix Chemie (BASF)) | 0.2 |
| Vitamin E (BASF) | 0.10 |
| Phosphoric acid (Phosphoric acid solution, BIESTERFELD (BCD-CHEMIE)) | Qs pH 2.2 |
| Demineralized water | Qs 100 |

The level of hydrogen peroxide is subsequently described in active percent levels, which takes into account that a 50% solution is used within the formulation B.

At the time of use, one part by weight of composition A1 is mixed with one part by weight of composition B. One part by weight of composition A2 is mixed with one part by weight of composition B. One part by weight of composition A3 is mixed with one part by weight of composition B.

The mixture is applied to tresses made of natural white hair (Kerling International Haarfabrik GmbH, "Greifsträhnen remis aus weißen"). 4 grams of the mixed composition is applied to each gram of tress, with the composition thoroughly worked into the tress. The tresses are then placed into an oven at 30° C. and left for 35 min. The tresses are then removed and rinsed for 2 min and then washed twice with a standard shampoo and then dried.

The color of the tresses is measured using a Minolta 2600d spectrophotometer. The tress is measured at five points, on both the front and the back side of the hair tress. The total of 10 data points for each tress are converted into L*a*b values assuming D65 lighting and a 10° Observer. The Chroma C is given by the following expression using the values of a* and b obtained in the L*a*b measurements.

$$C=\sqrt{(a^2+b^2)}$$

Results Chromaticity:

|  | a* | b | C* |
|---|---|---|---|
| Composition A1 + B (comparative composition) | 3.6 | −3.8 | 5.2 |
| Composition A2 + B | 3.75 | −7.0 | 7.9 |
| Composition A3 + B | 4.5 | −13.0 | 11.9 |

When the agent resulting from the mixture of the dye composition and the oxidizing composition comprises a concentration of alkalizing agent of not more than 1.75% by weight relative to the total weight of the mixture, we acknowledge that composition A2+B and composition A3+B, i.e. compositions according to the invention, present an increase of chromaticity which results on a wider range of colors obtained.

Moving from the mixture of compositions A2+B through to the mixture of compositions A3+B result in a series of blue/violet colors with increasing chromaticity.

Thus, even if the concentration of alkalizing agent is decreased compare to comparative composition (i.e. A1+B), the inventors have surprisingly found that the chromaticity of the colors on the hair is increased and new shades of colors are obtained.

Example 2

The following dye composition is prepared (in the table below, the amounts are expressed in grams). The dye composition corresponds to compositions C1 to C3.

|  | Composition C1 Amount (% w/w) | Composition C2 Amount (% w/w) | Composition C3 Amount (% w/w) |
| --- | --- | --- | --- |
| Liquid petroleum jelly | 55 | 55 | 55 |
| Octyldodecanol | 10 | 10 | 10 |
| Oleyl alcohol (10 OE) | 5 | 5 | 5 |
| Distearyldimethylammonium-modified hectorite | 1.5 | 1.5 | 1.5 |
| N,N-bis(2-hydroxyethyl)-p-phenylenediamine | 0.55 | 0.55 | 0.55 |
| Naphthol | 1.8 | 1.8 | 1.8 |
| Ascorbic acid | 0.25 | 0.25 | 0.25 |
| Propylene carbonate | 0.5 | 0.5 | 0.5 |
| Propylene glycol | 2 | 2 | 2 |
| Ethanol | 2.5 | 2.5 | 2.5 |
| Monoethanolamine | 4.5 | 3.25 | 2.0 |
| Hexylene glycol | 1 | 1 | 1 |
| Dipropylene glycol | 1 | 1 | 1 |
| POE/POP/POE (Poloxamer 184) | 9 | 9 | 9 |
| Diethylenetriaminepentaaectic acid | 1 | 1 | 1 |
| Sodium hydroxide | 0.4 | 0.4 | 0.4 |
| Demineralized water | Qs 100 | Qs 100 | Qs 100 |

Different amounts of alkalinizing agent, which is monoethanolamine, are tested in compositions C1 through to C3.

The oxidizing composition corresponds to composition B in accordance with the present invention.

| Composition B | Amount (% w/w) |
| --- | --- |
| Liquid petroleum jelly | 20 |
| Cetearyl alcohol | 8 |
| Oxyethylenated cetylstearyl alcohol (33 OE) | 3 |
| Glycerol | 0.5 |
| Hydrogen peroxide | 12 |
| Sodium stannate | 0.04 |
| Tetrasodium pyrophosphate | 0.03 |
| Polyquaternium-6 | 0.2 |
| Vitamin E | 0.10 |
| Phosphoric acid | Qs pH 2.2 |
| Demineralized water | Qs 100 |

The level of hydrogen peroxide is subsequently described in active percent levels, which takes into account that a 50% solution is used within the formulation B.

At the time of use, one part by weight of composition C1 is mixed with one part by weight of composition B. One part by weight of composition C2 is mixed with one part by weight of composition B. One part by weight of composition C3 is mixed with one part by weight of composition B.

The mixture is applied to tresses made of natural white hair (Kerling International Haarfabrik GmbH, "Greifsträhnen remis aus weißen").

4 grams of the mixed composition is applied to each gram of tress, with the composition thoroughly worked into the tress. The tresses are then placed into an oven at 30° C. and left for 35 min. The tresses are then removed and rinsed for 2 min and then washed twice with a standard shampoo and dried.

The color of the tresses is measured using a Minolta 2600d spectrophotometer. The tress is measured at five points, on both the front and the back side of the hair tress. The total of 10 data points for each tress are converted into L*a*b values assuming D65 lighting and a 10° Observer.

Results Chromaticity:

|  | a* | b | C |
| --- | --- | --- | --- |
| Composition C1 + B (comparative composition) | −4.8 | −13.3 | 14.1 |
| Composition C2 + B | −4.9 | −16.1 | 16.8 |
| Composition C3 + B | −5.01 | −19.4 | 20.0 |

When the agent resulting from the mixture of the dye composition and the oxidizing composition comprises a concentration of alkalizing agent of not more than 1.75% by weight relative to the total weight of the mixture, we acknowledge that composition C2+B and composition C3+B, i.e. compositions according to the invention, present an increase of chromaticity which results on a wider range of colors obtain.

Moving from the mixture of compositions C2+B through to the mixture of compositions C3+B result in a series of blue/green colors with increasing chromaticity.

Example 3

The following dyeing composition is prepared (in the table below, the amounts are expressed in grams). The dye composition corresponds to compositions D1 to D3.

|  | Composition D1 Amount (% w/w) | Composition D2 Amount (% w/w) | Composition D3 Amount (% w/w) |
|---|---|---|---|
| Liquid petroleum jelly | 55 | 55 | 55 |
| Octyldodecanol | 10 | 10 | 10 |
| Oleyl alcohol (10 OE) | 5 | 5 | 5 |
| Distearyldimethylammonium-modified hectorite | 1.5 | 1.5 | 1.5 |
| Toluene-2,5-diamine sulfate | 0.275 | 0.275 | 0.275 |
| Resorcinol | 0.138 | 0.138 | 0.138 |
| Ascorbic acid | 0.25 | 0.25 | 0.25 |
| Propylene carbonate | 0.5 | 0.5 | 0.5 |
| Propylene glycol | 2 | 2 | 2 |
| Ethanol | 2.5 | 2.5 | 2.5 |
| Monoethanolamine | 4.5 | 3.25 | 2.0 |
| Hexylene glycol | 1 | 1 | 1 |
| Dipropylene glycol | 1 | 1 | 1 |
| POE/POP/POE (Poloxamer 184) | 9 | 9 | 9 |
| Diethylenetriaminepentaacetic acid | 1 | 1 | 1 |
| Sodium hydroxide | 0.4 | 0.4 | 0.4 |
| Demineralized water | Qs 100 | Qs 100 | Qs 100 |

Different amounts of alkalinizing agent, which is monoethanolamine, are tested with compositions D1 to D3.

The oxidizing composition corresponds to composition B in accordance with the present invention.

| Composition B | Amount (% w/w) |
|---|---|
| Liquid petroleum jelly | 20 |
| Cetearyl alcohol | 8 |
| Oxyethylenated cetylstearyl alcohol (33 OE) | 3 |
| Glycerol | 0.5 |
| Hydrogen peroxide | 12 |
| Sodium stannate | 0.04 |
| Tetrasodium pyrophosphate | 0.03 |
| Polyquaternium-6 | 0.2 |
| Vitamin E | 0.10 |
| Phosphoric acid | Qs pH 2.2 |
| Demineralized water | Qs 100 |

The level of hydrogen peroxide is subsequently described in active percent levels, which takes into account that a 50% solution is used within the formulation B.

At the time of use, one part by weight of composition D1 is mixed with one part by weight of composition B. One part by weight of composition D2 is mixed with one part by weight of composition B. One part by weight of composition D3 is mixed with one part by weight of composition B.

The mixture is applied to tresses made of natural white hair (Kerling International Haarfabrik GmbH, "Greifsträhnen remis aus weißen"). 4 grams of the mixed composition is applied to each gram of tress, with the composition thoroughly worked into the tress. The tresses are then placed into an oven at 30 C and left for 35 min. The tresses are then removed from the oven and rinsed for 2 min and then washed twice with a standard shampoo and then dried.

The color of the tresses is measured using a Minolta 2600d spectrophotometer. The tress is measured at five points, on both the front and the back side of the hair tress. The total of 10 data points for each tress are converted into $L^*a^*b$ values assuming D65 lighting and a 10° Observer.

Results Chromaticity:

|  | a* | b | C |
|---|---|---|---|
| Composition D1 + B (comparative composition) | 3.2 | 17.8 | 18.1 |
| Composition D2 + B | 3.1 | 17.9 | 18.2 |
| Composition D3 + B | 2.9 | 18.3 | 18.5 |

When the agent resulting from the mixture of the dye composition and the oxidizing composition comprises a concentration of alkalizing agent of not more than 1.75% by weight relative to the total weight of the mixture, we acknowledge that composition D2+B and composition D3+B, i.e. compositions according to the invention, present an increase of chromaticity which results on a wider range of colors obtain.

Moving from the mixture of compositions D2+B through to the mixture of compositions D3+B result in a series of yellow colors with increasing chromaticity.

Thus, even if the concentration of alkalizing agent is decreased compare to comparative composition (i.e. composition D1+B), the inventors have surprisingly found that the chromaticity of the colors on the hair is increased and new shades of colors are obtained.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All publications, patents and patent applications are incorporated herein by reference. While in the foregoing specification this invention has been described in relation to certain embodiments (hereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An agent for dyeing keratin fibers, the agent comprising:
    a composition A comprising at least one alkalizing agent, at least one oxidative dye precursor, at least one surfactant and at least one fatty substance which is free of carboxyl anions, and free of carboxylic acid groups, the composition A having a pH in a range of from 3 to 12, and
    a composition B comprising at least one oxidizing agent and at least one surfactant, wherein the concentration of fatty substance is free of carboxyl anions, and free of carboxylic acid groups after mixing composition A and composition B, and is at least 20% by weight relative to the total weight of the mixed composition A and B, the composition B having a pH of less than 7, and wherein the concentration of alkalizing agent after extemporaneous or successive mixing of composition A and composition B is in range of 1.0% to 1.65% by weight relative to the total weight of the mixed composition A and B and at least one of composition A, composition B, or both comprises a buffering agent.

2. An agent for dyeing keratin fibers according to claim 1, characterized in that the alkalising agent is monoethanolamine (MEA).

3. An agent for dyeing keratin fibers according to claim 1, characterized in that composition A comprises a total amount of alkalizing agent ranging from 0.1% to 3.5% by weight relative to the total weight of the composition A.

4. An agent for dyeing keratin fibers according to claim 1, characterized in that composition A comprises a total amount of alkalizing agent of less than 3.5% by weight relative to the total weight of the composition A.

5. An agent for dyeing keratin fibers according to claim 1, characterized in that the oxidative dye precursors comprises at least one primary intermediate selected from the group consisting of toluene-2,5-diamine, 2-methoxymethyl-p-phenylenediamine, N,N-bis(2-hydroxyethyl)-p-phenylenediamine, p-aminophenol and mixtures thereof, and at least one coupler selected from resorcinol, methyl-resorcinol, naphthol, m-aminophenol and mixtures thereof.

6. An agent for dyeing keratin fibers according to claim 1, characterized in that the fatty substances free of carboxylic acid groups are selected from the group consisting of liquid paraffins, liquid petroleum jelly, polydecenes, liquid fatty acid esters, liquid fatty alcohols, and mixtures thereof.

7. An agent for dyeing keratin fibers according to claim 1, characterized in that the composition A comprises an amount of fatty substances free of carboxylic acid groups of greater than 25% by total weight of composition A.

8. An agent for dyeing keratin fibers according to claim 1, characterized in that the composition B comprises an amount of fatty substances free of carboxylic acid groups of greater than 10% by total weight of composition B.

9. An agent for dyeing keratin fibers according to claim 1, characterized in that the surfactants are selected from the group consisting of non-ionic surfactants, anionic surfactants and mixtures thereof.

10. An agent for dyeing keratin fibers according to claim 1, characterized in that the surfactants are selected from the group consisting of polyoxyethylene (POE)/polyoxypropylene(POP)/polyoxyethylene(POE) units, oxyethylenated $C_8$-$C_{30}$ alcohols, and mixtures thereof.

11. An agent for dyeing keratin fibers according to claim 1, characterized in that the oxidizing agent is selected from the group consisting of hydrogen peroxide, percarbonates, persulphates, and mixtures thereof.

12. Process for dyeing keratin fibers, comprising the application to the wet or dry fibers, of the agent obtained by mixing of composition A and composition B as defined in claim 1.

13. Process for dyeing keratin fibers, comprising the application to the wet or dry fibers of a composition obtained by extemporaneous mixing of composition A and composition B as defined in claim 1.

14. Kit for dyeing keratin fibers, comprising the agent of claim 1, wherein a first compartment contains composition A and a second compartment contains composition B.

15. An agent for dyeing keratin fibers according to claim 3, characterized in that composition A comprises a total amount of alkalizing agent ranging from 0.5% to 3.25% by weight.

16. An agent for dyeing keratin fibers according to claim 7, characterized in that the composition A comprises an amount of fatty substances free of carboxylic acid groups of greater than 30%.

17. An agent for dyeing keratin fibers according to claim 8, characterized in that the composition B comprises an amount of fatty substances free of carboxylic acid groups of greater than 15% by total weight of composition B.

18. An agent for dyeing keratin fibers according to claim 11, characterized in that the oxidizing agent is hydrogen peroxide.

* * * * *